000
(12) United States Patent
Han et al.

(10) Patent No.: US 9,233,129 B2
(45) Date of Patent: Jan. 12, 2016

(54) METHOD FOR PURIFYING BEE VENOM ON MASS SCALE

(71) Applicant: Republic of Korea (Management:Rural Development Administration), Suwon, Gyeongg-Do (KR)

(72) Inventors: Sang Mi Han, Chungcheongnam-Do (KR); Kwang Gill Lee, Gyeonggi-Do (KR); Kwan Kyu Park, Daegu (KR)

(73) Assignee: Republic of Korea (Management: Rural Development Administration), Suwon, Gyeonggi-Do (KR)

( * ) Notice: Subject to any disclaimer, the term of this patent is extended or adjusted under 35 U.S.C. 154(b) by 0 days.

(21) Appl. No.: 14/322,400

(22) Filed: Jul. 2, 2014

(65) Prior Publication Data

US 2014/0314871 A1  Oct. 23, 2014

Related U.S. Application Data

(63) Continuation of application No. PCT/KR2012/003139, filed on Apr. 24, 2012.

(30) Foreign Application Priority Data

Jan. 4, 2012 (KR) .................. 10-2012-0001015

(51) Int. Cl.
*A61K 35/644* (2015.01)
*A61K 35/64* (2015.01)
(Continued)

(52) U.S. Cl.
CPC ............. *A61K 35/642* (2013.01); *A23L 1/0152* (2013.01); *A23L 1/0156* (2013.01); *A23L 1/076* (2013.01);
(Continued)

(58) Field of Classification Search
USPC .......................................................... 424/539
IPC ......................................... A61K 35/642,35/644
See application file for complete search history.

(56) References Cited

U.S. PATENT DOCUMENTS 2,112,828 A * 4/1938 Buhler ........................ 424/537
5,451,660 A * 9/1995 Builder et al. ............... 530/344
(Continued)

FOREIGN PATENT DOCUMENTS

| CN | 101088514 | * 12/2007 |
| CN | 101089017 | * 12/2007 |

(Continued)

OTHER PUBLICATIONS

He et al. Chromatographia. 2007. vol. 65, No. 9/10, pp. 581-590.*
(Continued)

*Primary Examiner* — Chris R Tate
(74) *Attorney, Agent, or Firm* — Mintz Levin Cohn Ferris Glovsky and Popeo, P.C.; Kongsik Kim; Richard B. Emmons

(57) ABSTRACT

Disclosed is a method for the purification of bee venom on a mass scale. It comprises dissolving crude bee venom in a solvent to form a bee venom solution; applying an adsorbent to the bee venom solution to form a mixture; and removing the adsorbent through filtration to afford a pure bee venom solution. By the method of the present invention, crude bee venom collected from bee farms can be purified to a purity of 99% or higher on a mass scale, without inducing a change in the composition thereof, and thus the purified bee venom can be used as a material for medicines, cosmetics and foods.

1 Claim, 3 Drawing Sheets

(51) Int. Cl.
   *A23L 1/076*  (2006.01)
   *B01D 15/00*  (2006.01)
   *A23L 1/015*  (2006.01)
(52) U.S. Cl.
   CPC ................ *A61K 35/64* (2013.01); *B01D 15/00* (2013.01); *A23V 2300/14* (2013.01); *A23V 2300/30* (2013.01)

(56) References Cited

U.S. PATENT DOCUMENTS

2008/0248127 A1* 10/2008 Kim .............................. 424/539

2012/0082656 A1* 4/2012 Yoon et al. ................... 424/94.6

FOREIGN PATENT DOCUMENTS

| CN | 102526116 | * | 7/2012 |
| DE | 924582 | * | 3/1955 |
| KR | 100758814 | * | 9/2007 |
| KR | 20100125991 | * | 12/2010 |
| WO | WO 2010/134676 | * | 11/2010 |

OTHER PUBLICATIONS

Jentsch et al. Int. J. Peptide Proteins. 1977. vol. 9, pp. 78-79.*

* cited by examiner

FIG. 1

```
         ┌──────────┐
         │ Bee toxin│
         └────┬─────┘
              │ ←── water
S1            ▼
         ┌──────────┐
         │Dissolution│
         └────┬─────┘
              │ ←── Adsorbent
              ▼
         ┌──────────┐
S2       │Adsorption│
         └────┬─────┘
              ▼
         ┌──────────┐
S3       │Filtration│
         └────┬─────┘
              ▼
       ┌──────────────┐
       │Pure bee toxin│
       │   solution   │
       └──────────────┘
```

Before purification → After purification

Before purification    After purification

METHOD FOR PURIFYING BEE VENOM ON MASS SCALE

CROSS-REFERENCE TO RELATED APPLICATIONS

This is a continuation of International Application No. PCT/KR2012/003139 filed on Apr. 24, 2012, which claims priority to Korean Application No. 10-2012-0001015 filed on Jan. 4, 2012, which applications are incorporated herein by reference.

TECHNICAL FIELD

The present invention relates to a method for the purification of bee venom on a mass scale. More particularly, the present invention relates to a method for purifying bee venom without inducing a change in the composition thereof, thereby producing highly pure bee venom on a mass scale.

BACKGROUND ART

Bee venom refers to the toxic substance that is produced by workers bees and has been used in the therapy of diseases.

For the application of bee venom to the body, previously, worker bees which had been caught were forced to sting an affected site or only the stingers, after being detached from worker bees, were inserted into an affected site. However, it is difficult to control the injection amount or concentration of bee venom in this manner, which makes the objectification and generalization of the bee venom therapy impossible and may generate side effects such as shock.

If given the ability to adjust the amount and concentration of drug depending on the body condition and constitution of the patient, bee venom therapy can be safely used without inducing any side effects. Bee venom therapy has spread to some degree over the U.S. and the Europe. In the early 1990s, the subcutaneous injection of purified bee venom for the treatment of inflammation and pain was approved by the FDA, and it is produced under the brand name of Apitoxin. Recently, bee venom collectors have been located over a vast area in bee farms and thus, a large amount of bee venom is collected.

However, the bee venom collected via the collectors of bee farms contains significant amounts of contaminants such as dust, soil, etc., and impurities such as honey, pollen and propolis. These foreign materials change the composition of bee venom, degrading the physiological activity of bee venom.

SUMMARY

It is an object of the present invention to provide a method for purifying bee venom without inducing a change in the composition thereof, thereby producing highly pure bee venom on a mass scale.

The objects to be accomplished by the present invention are not limited to the above-mentioned object, and other objects that are not stated may be clearly understood to those having ordinary skill in the art from the following description.

In order to accomplish the above-mentioned object, the present invention provides a method for purifying bee venom on a mass scale, comprising: solubilizing crude bee venom in a solvent to form a bee venom solution; applying an adsorbent to the bee venom solution to form a mixture; and removing the adsorbent by filtration to afford a pure bee venom solution.

In one embodiment, the bee venom solution may be filtered before the adsorbent is applied thereto.

In this regard, the bee venom solution is filtered through filter paper which may preferably be a cellulose filter.

In the method, the solvent may be water.

According to another embodiment, the crude bee venom is used in an amount of from 0.02 to 0.1% by weight, based on a total weight of the bee venom solution.

In another embodiment, the adsorbent is PSA (primary secondary amine).

In another embodiment, the adsorbent is added in an amount of from 0.1 to 10 g per liter of the bee venom solution.

In another embodiment, the filtration for removing the absorbent may be vacuum filtration and may be conducted using filter paper which may preferably be a cellulose filter.

The method may further comprise filtering the pure bee venom solution to yield a filtrate and lyophilizing the filtrate to produce a fine powder.

In this regard, the filtering step is conducted by vacuum filtration.

According to another embodiment, the lyophilizing step is conducted at −20° C. or lower.

By the method of the present invention, crude bee venom collected from bee farms can be purified to a purity of 99% or higher on a mass scale, without inducing a change in the composition thereof, and thus the purified bee venom can be used as a material for medicines, cosmetics and foods.

BRIEF DESCRIPTION OF DRAWINGS

FIG. 1 is a flow chart illustrating a method for purifying bee venom on a large scale according to the present invention.

DETAILED DESCRIPTION

Figure 2:
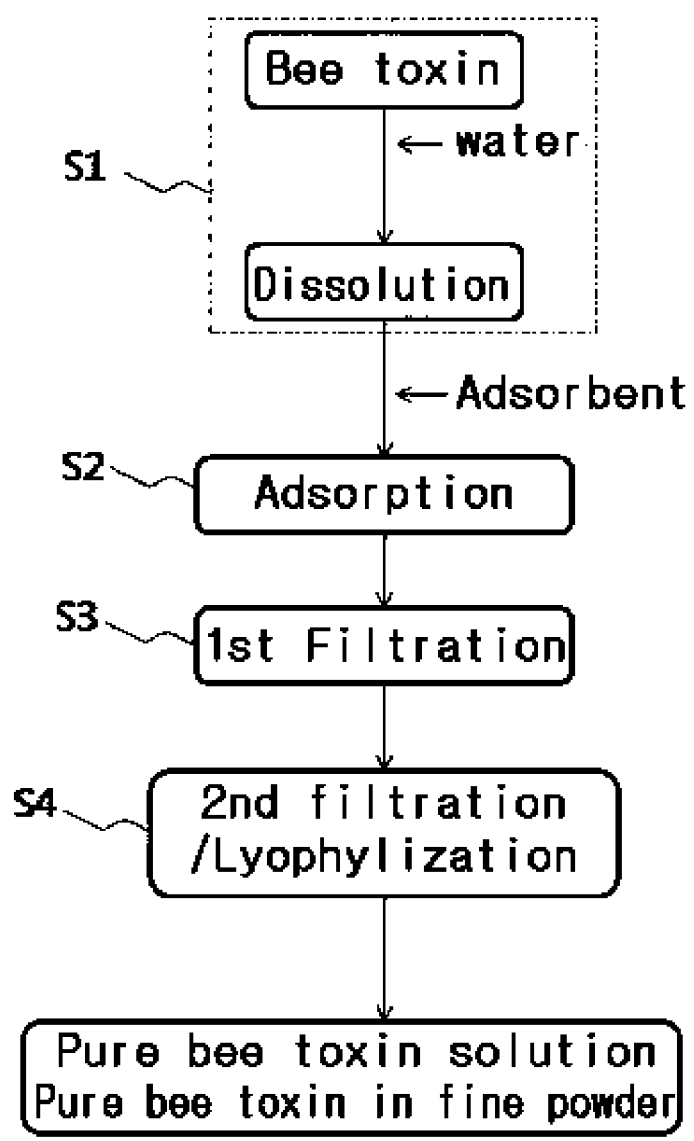
FIG. 2 is a flow chart illustrating a method for purifying bee venom on a large scale to produce pure bee venom as a fine powder suitable for storage for a long period of time in accordance with the present invention.

Below, a description will be given of preferred embodiments of the present invention in conjunction with the accompanying drawings. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present invention, the description thereof will be omitted.

With reference to FIG. 1, there is a flow chart illustrating a method for purifying bee venom on a mass scale.

As seen in the flow chart, the purification method of the present invention starts with the dissolution of collected bee venom (crude bee venom) (S1).

In step S1, crude bee venom is dissolved to give a bee venom solution. Preferably, crude bee venom is dissolved in water.

Being almost completely water soluble, bee venom is dissolved in water whereas non-water soluble foreign substances remain undissolved.

In this regard, water-soluble bee venom is preferably dissolved in deionized water so as to minimize the contamination stemming from the solvent.

Preferably, the amount of crude bee venom that is dissolved varies from 0.02 to 0.1% by weight, based on the total weight of the bee venom solution. For example, when the amount of bee venom is below 0.02% by weight, there is not enough to expect the effects of bee venom. On the other hand, an amount of bee venom exceeding 0.1% by weight is in a state of over-saturation, which is economically unfavorable.

Optionally, the bee venom solution may be subjected to a filtration process.

This filtration is used to remove non-water-soluble impurities (sand, soil, bee glue, pollen, etc.) and may be conducted using filter paper. Preferably, the filter paper may be a cellulose filter.

Having a particle size of from 20 to 30 µm, the non-water-soluble foreign substance is filtered out by filter paper such as a cellulose filter.

In step S2, water-soluble foreign substances are removed by adsorption. For this, an adsorbent is added to the bee venom solution.

That is, after the removal of non-water soluble foreign substances, the water-soluble foreign substances, such as honey or pigment, which have dissolved in the bee venom solution, are removed by adsorption.

For this, an adsorbent is added and mixed homogeneously to remove the water-soluble foreign substances which remain dissolved in the solution.

So long as it adsorbs water-soluble foreign substances, such as pigments, any adsorbent may be used in the present invention. Preferred is PSA (primary secondary amine), which is one of the most potent adsorbents known to date.

The adsorbent may be preferably added in an amount of from 0.1 to 10 g per liter of the bee venom solution. When the amount of the adsorbent is less than 0.1 g per liter of the bee venom solution, the adsorption ability is too poor to separate pure bee venom. An amount of the adsorbent exceeding 10 g per liter causes a change in composition, making it difficult to separate bee venom at a purity of 99% or higher.

In step S3, the mixture is filtered to separate pure bee venom from the adsorbent and foreign substances adsorbed to the adsorbent, whereby bee venom can be purified on a mass scale.

The filtration is preferably vacuum filtration which is more preferably preformed using filter paper, in order to afford bee venom at a purity of 99% or higher.

In this context, the adsorbent to which the water-soluble foreign substances have adhered (particle retention (liquid)) ranges in size from 0.45 to 0.8 µm, and the filter paper is preferably a cellulose filter which is suitable for filtering out the adsorbent.

Turning to FIG. 2, there is a flow chart illustrating a method for purifying bee venom on a mass scale in the form of fine powder in another embodiment of the present invention, whereby it can be stored for a long period of time.

In addition to the purification procedure (S1, S2 and S3) of FIG. 1, as seen in this flow chart, the purification method according to this embodiment of the present invention comprises a step of secondary filtration and freeze drying (S4) by which the pure bee venom is produced as a fine powder free of bacteria and fungi and thus can be used as a material for medicines, cosmetics and foods and be stored for a long period of time.

The secondary filtration is preferably vacuum filtration which utilizes filter paper and more preferably a cellulose filter with a pore size of 0.2 µm or smaller. The resulting filtrate is lyophilized at −20° C. or colder to produce pure bee venom as a powder.

As described above, the purification method of the present invention can remove foreign substance from crude bee venom without inducing a change in the composition of bee venom to produce bee venom at a purity of 99% or higher on a mass scale, which can be used as a material for medicines, cosmetics and foods.

EXAMPLES

A better understanding of the present invention may be obtained through the following examples which are set forth to illustrate, but are not to be construed as limiting the present invention.

Example 1

Purification of Bee Venom 1

1. Removal of Non-Water-Soluble Foreign Substances

1). The crude bee venom collected using bee venom collectors was treated under the following conditions to dissolve its water-soluble components in water.

Conditions and Methods a. Solvent: deionized water b. Bee venom content: 0.02~0.1% by weight (based on total weight)

c. Time: Bee venom was lightly stirred for 15 sec in the solvent using a glass rod.

2) After the water-soluble ingredients were dissolved in such a manner, the solution was filtered through filter paper under the following conditions. The filtrate was used in the next step whereas non-water-soluble foreign impurities such as sand, soil, bee glue, pollen, etc. were left behind on the filter paper and discarded.

Filter Paper

Type: cellulose filter (glass microfiber filter is excluded from being used)

Particle retention (liquid): 20~30 µm

Air flow rate: 5~10 s/100 mL/in$^2$

2 Removal of Water-Soluble Foreign Impurities

1) After the removal of non-water-soluble foreign impurities, the water-soluble foreign impurities which have dissolved in water were removed in the presence of a primary secondary amine (PSA) under the following conditions.

Conditions and Method a. The bee venom solution was added to a beaker containing primary secondary amine.

b. The solution was stirred to allow ingredients other than sugars and bee venom to be adsorbed to the adsorbent, followed by the separation of pure bee venom using filter paper.

c. Loading rate: Primary secondary amine was used in an amount of 0.11 g per liter of the bee venom solution.

2) After the removal of water-soluble foreign impurities, vacuum filtration was conducted using filter paper under the following conditions to afford bee venom 99% pure.

Filter Paper type: cellulose filter particle retention (liquid): 0.45~0.8 µm

Example 2

Purification of Bee Venom 2

The pure bee venom solution was sterilized by removing bacteria and fungi through vacuum filtration, after which the germ-free solution was lyophilized to produce a fine powder which can be used as a material for medicines, cosmetics and foods and can be stored for a long period of time.

1) The pure bee venom solution prepared in Example 1 was vacuum filtered using filter paper under the following condition.

Filter Paper
type: cellulose filter
particle retention (liquid): 0.2 μm

2) After vacuum filtration, the filtrate was freeze-dried under the following condition to produce pure bee venom as a fine powder.

Lyophilization Condition
Temperature: −20° C. or below

Because bee venom powder would fly away due to its lightness after lyophylization, the filtrate had to be placed into a lyophilizer as it was contained within a container with fine holes and covered with a lid. Lyophilization was conducted to complete dryness.

Test Example 1

Qualitative and Quantitative Analysis of Main Components

To examine the purity and ingredient of the pure bee venom solution of Example 1, liquid chromatography was conducted under the following conditions.

Conditions and Method
1) Column: Sepadex 200
2) Elution buffer: 0.1 M ammonium formate
3) Ingredients to be analyzed: melittin, apamin, phospholipase A2
4) Qualitative and quantitative analysis was performed with reference to a standard.
5) It was determined as being 99% pure bee venom when the components were detected as shown in Table 1.

TABLE 1

| Main Ingredient | Pure bee venom |
| --- | --- |
| Apamine | 2.8 ± 0.9 |
| Phospholipase $A_2$ | 12.8 ± 2.6 |
| Melittin | 50.7 ± 8.9 |

Test Example 2

Comparison of Contents of Main Components

Contents of the main ingredients of bee venom were compared using liquid chromatography under the following condition.
1) Column: Sepadex TM75
2) Elution buffer: Ammonium formate
3) Injection Volume: 100 μl (0.1 mg/ml)

Figure 3:
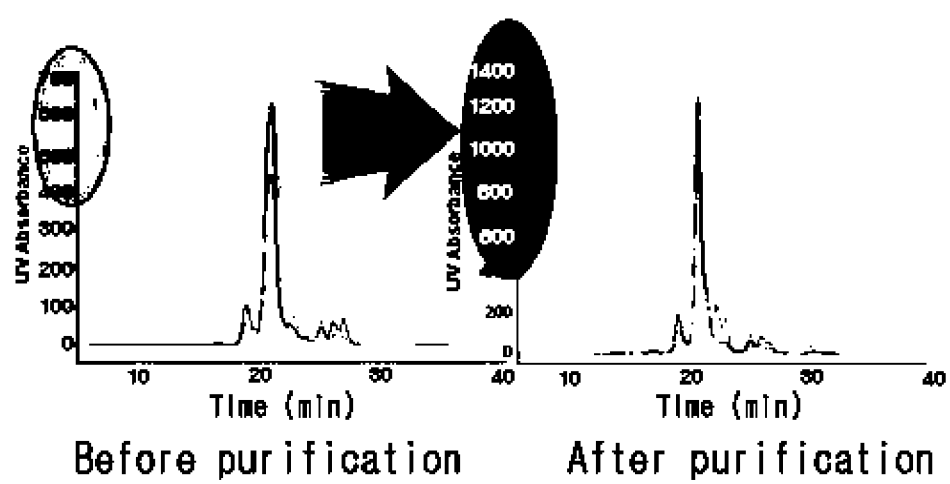
FIG. 3 shows chromatograms comparing the contents of main ingredients of bee venom before and after purification.
A: before purification, B: after purification
Figure 4:
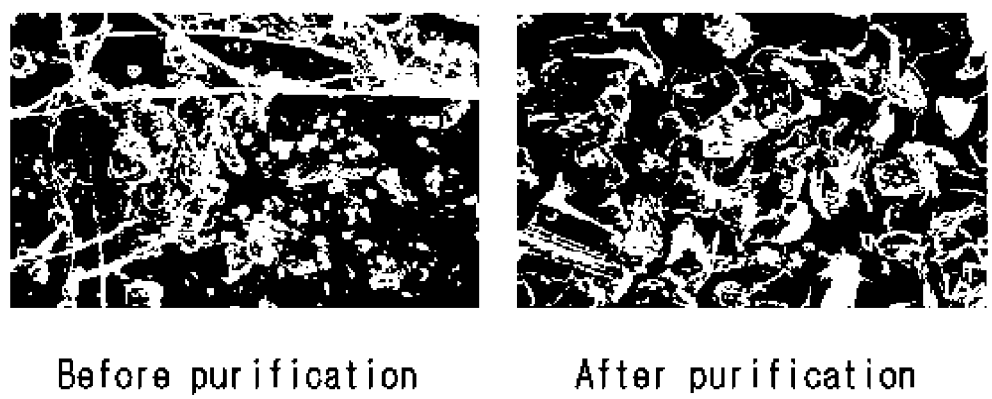
FIG. 4 shows electron microphotographs of bee venom before and after purification.
A: before purification, B: after purification

As can be seen in FIGS. 3 and 4, the crude bee venom contained bee venom in an amount of 50% by weight or less, but was found to be purified to the purity of 99% by the purification method of the present invention.

Test Example 3

Antibacterial Activity

To evaluate the purification method, the purified bee venom was assayed for antibacterial activity.

Method
1) Test strain: *Staphylococcus aureus, Propionibacterium.acne*
2) Assay: MIC and MBC assay
3) The bee venom was determined as being pure when it exhibited the MIC and MBC values shown in Table 2.

TABLE 2

| Bacteria | MIC(μg/ml) | MBC(μg/ml) |
| --- | --- | --- |
| *Staphylococcus aureus* | 0.1~0.2 | 0.2~0.4 |
| *Propionibacterium acne* | 0.05~0.1 | 0.1~0.2 |

Taken together, the data obtained above indicate that the purification method of the present invention can purify crude bee venom collected from bee farms to a purity of 99% or higher.

Accordingly, bee venom with a purity of 99% or higher can be produced on a mass scale by the method of the present invention and is useful as a material for medicines, cosmetics and foods.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements.

The invention claimed is:

1. A method for producing purified bee venom on a mass scale, comprising:

dissolving crude bee venom in water to form a bee venom solution, wherein the crude bee venom is present in the solution in an amount of 0.02-0.1 wt %;

filtering the bee venom solution through a cellulose filter paper having a particle size of 20-30 μm under reduced pressure to remove non-water-soluble impurities;

applying an absorbent to the filtered bee venom solution at a level of 0.1 to 10 g per liter of the bee venom solution to form a mixture, wherein the absorbent is a primary and secondary amine (PSA);

removing the absorbent by filtering the mixture through a cellulose filter paper having a particle size of 0.45-0.8 μm, followed by filtering the mixture again through a cellulose filter paper having a particle size of 0.2 μm under vacuum, to produce a purified bee venom solution free of water-soluble foreign impurities; and lyophilizing the purified bee venom solution at −20° C. or less to obtain said purified bee venom, wherein the purified bee venom is 99% pure.

* * * * *